United States Patent
Yin et al.

(10) Patent No.: US 10,073,068 B2
(45) Date of Patent: Sep. 11, 2018

(54) LIQUID CHROMATOGRAPHY COLUMNS WITH STRUCTURED WALLS

(71) Applicant: AGILENT TECHNOLOGIES, INC., Santa Clara, CA (US)

(72) Inventors: Hongfeng Yin, Cupertino, CA (US); Reid A. Brennen, San Francisco, CA (US); Eric Lyster, Oakland, CA (US); Roger Slocum, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/023,240

(22) PCT Filed: Aug. 19, 2014

(86) PCT No.: PCT/US2014/051708
§ 371 (c)(1),
(2) Date: Mar. 18, 2016

(87) PCT Pub. No.: WO2015/047598
PCT Pub. Date: Apr. 2, 2015

(65) Prior Publication Data
US 2016/0231293 A1    Aug. 11, 2016

Related U.S. Application Data

(60) Provisional application No. 61/879,485, filed on Sep. 18, 2013.

(51) Int. Cl.
*G01N 30/60* (2006.01)

(52) U.S. Cl.
CPC ....... *G01N 30/606* (2013.01); *G01N 30/6065* (2013.01); *G01N 30/6086* (2013.01)

(58) Field of Classification Search
CPC ............ G01N 30/606; G01N 30/6065; G01N 30/6086
(Continued)

(56) References Cited

U.S. PATENT DOCUMENTS 3,250,395 A * 5/1966 Blume ............... G01N 30/6026
                                                210/198.2
3,522,172 A * 7/1970 Pretorius et al. ...... G01N 30/38
                                                210/198.2
(Continued)

FOREIGN PATENT DOCUMENTS

CN      1366180 A     8/2002
CN    101271091 A     9/2008
(Continued)

OTHER PUBLICATIONS

International Search Report and Written Opinion dated Mar. 27, 2015 for related International Application No. PCT/US2014/051708.
(Continued)

*Primary Examiner* — Robert R Raevis

(57) ABSTRACT

A liquid chromatography (LC) column includes a wall having a length along a central axis from the inlet end to the outlet end, the wall enclosing a column interior and having a column radius relative to the central axis, the wall comprising a structured portion configured such that the column radius varies along the length; and a plurality of particles packed in the column interior, wherein at least some of the particles are in contact with the structured portion.

8 Claims, 10 Drawing Sheets

(58) Field of Classification Search
USPC ........ 73/863.21, 23.39, 61.53; 210/656–659; 422/70, 89
See application file for complete search history.

(56) References Cited

U.S. PATENT DOCUMENTS

| | | | | |
|---|---|---|---|---|
| 4,059,523 | A | * | 11/1977 | Mochizuki ............. G01N 30/56 210/198.2 |
| 4,250,035 | A | * | 2/1981 | McDonald ............. B01D 15/08 206/305 |
| 4,692,243 | A | | 9/1987 | Porsch et al. |
| 4,787,971 | A | * | 11/1988 | Donald ................. B01D 15/22 210/198.2 |
| 5,908,172 | A | * | 6/1999 | Pierro .................... B65H 75/14 242/118.4 |
| 5,908,552 | A | * | 6/1999 | Dittman ........... G01N 27/44704 204/601 |
| 6,207,049 | B1 | | 3/2001 | Abdel-Rahman |
| 2002/0008058 | A1 | | 1/2002 | Nugent |
| 2006/0000238 | A1 | | 1/2006 | Griffin et al. |
| 2009/0065415 | A1 | | 3/2009 | Vetter et al. |
| 2009/0266752 | A1 | | 10/2009 | Hochgraeber et al. |

FOREIGN PATENT DOCUMENTS

| | | |
|---|---|---|
| CN | 102812354 A | 12/2012 |
| CN | 203002025 U | 6/2013 |
| EP | 0386925 A1 | 9/1990 |
| EP | 0779512 A1 | 6/1997 |
| EP | 1916522 A1 | 4/2008 |
| EP | 1244507 B1 | 3/2011 |
| EP | 2375421 A2 | 10/2011 |
| EP | 2597460 A1 | 5/2013 |
| WO | 8707526 A1 | 12/1987 |

OTHER PUBLICATIONS

Extended European Search Report dated Mar. 14, 2017 from related European Application No. 14849464.4.
Razing et a., "A system and columns for capillary HPLC" American Laboratory, May 2001.
Chinese Office action dated Mar. 23, 2017 from related Chinese Application No. 201480051377.8.

* cited by examiner

LIQUID CHROMATOGRAPHY COLUMNS WITH STRUCTURED WALLS

RELATED APPLICATIONS

This application is the national stage of International Application No. PCT/US2014/051708, filed Aug. 19, 2014, titled "LIQUID CHROMATOGRAPHY COLUMNS WITH STRUCTURED WALLS," which claims the benefit of U.S. Provisional Patent Application Ser. No. 61/879,485, filed Sep. 18, 2013, titled "LIQUID CHROMATOGRAPHY COLUMNS WITH STRUCTURED WALLS," the contents of both of which are incorporated by reference herein in their entireties.

TECHNICAL FIELD

The present invention relates generally to liquid chromatography (LC), and in particular to LC columns and methods for their fabrication.

BACKGROUND

Liquid chromatography (LC) is a technique for performing analytical or preparative separation of a liquid-phase sample material of interest (e.g., a mixture of different chemical compounds) into constituent components. During the course of a chromatographic separation, the sample material is transported in a mobile phase (typically one or more solvents). The sample/mobile phase is forced through a stationary phase that is immiscible with the mobile phase. Typically, the stationary phase is provided in the form of a mass of particles (a packing or bed) supported in a column or cartridge through which the sample flows. The column bed is typically retained at each end of the column by a frit or filter that allows the sample/mobile phase to flow through while preventing the packing material from escaping the column. The inlet end of the column is connected to an inlet conduit by which the sample/mobile phase is introduced into the column. A mobile phase reservoir, a pump and a sample injector are located upstream of the inlet end and interconnected to the inlet end via the inlet conduit. The outlet end of the column is connected via an outlet conduit to a suitable detector or other destination. In the column, the respective compositions of the mobile phase and stationary phase are selected to cause differing components of the sample material in the column to become distributed between the mobile phase and stationary phase to varying degrees dependent on the respective chemistries of the sample material's components. Components that are strongly retained by the stationary phase travel slowly with the mobile phase, while components that are weakly retained by the stationary phase travel more rapidly. As a result, components of differing compositions become separated from each other as the mobile phase flows through the column. In this manner, the components are in effect sorted sequentially as the eluent flows out from the column, thereby facilitating their analysis by the detector or otherwise isolating components of interest from other components of the original sample material.

Conventionally, the inside wall surface of an LC column is made as smooth as possible. This also means that the inside surface remains at a constant radial position relative to the column center (the central axis through the column) over the length of the column, such that the inside surface is parallel to the net fluid flow direction through the column. In other words, the wall defining the interior of the column is a straight cylindrical bore. This conventional configuration allows the particles to move easily along the inside wall surface during packing of the column and during any resettling of the column during the packing process. The disadvantage of this approach is that the packed particles are very ordered at and near the column wall while they are more randomly packed away from the column wall. As particles are packed into the column, they are forced outward toward the column wall. The restriction presented by the column wall thus results in a large number of particles being aligned at the same radial position from the column center. This leads to differing flow rates near and far from the column walls. This flow heterogeneity increases the rate of analyte dispersion and consequently reduces resolution of the detected peaks eluted from the column.

Therefore, there is a need for LC columns structured to reduce position-dependent flow heterogeneity in the columns.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a liquid chromatography (LC) column includes: a wall having a length along a central axis from the inlet end to the outlet end, the wall enclosing a column interior and having a column radius relative to the central axis, the wall comprising a structured portion configured such that the column radius varies along the length; and a plurality of particles packed in the column interior, wherein at least some of the particles are in contact with the structured portion.

According to another embodiment, a liquid chromatography (LC) column includes: an inlet end; an outlet end; a wall having a length along a central axis from the inlet end to the outlet end, the wall enclosing a column interior and having a column radius relative to the central axis, the wall comprising a main portion having a first radius, and a structured portion having a second radius different from the first radius, wherein the column radius varies along the length; and a plurality of particles packed in the column interior, wherein at least some of the particles are in contact with the structured portion and other particles are in contact with the main portion.

According to another embodiment, a method for fabricating a liquid chromatography (LC) column includes: forming a wall comprising an inlet end, an outlet end, and a length along a central axis from the inlet end to the outlet end, wherein the wall encloses a column interior and has a column radius relative to the central axis; forming a structured portion on the wall facing the column interior, wherein the structured portion is configured such that the column radius varies along the length; and forming a packing of particles in the column interior, wherein at least some of the particles are in contact with the structured portion.

According to another embodiment, a liquid chromatography system includes an LC column structured according to any of the embodiments disclosed herein. The inlet end and outlet end of the column may communicate with respective fluid lines. As examples, the inlet end may communicate with a sample source, and the outlet end may communicate with a detector configured for detecting peaks eluting from the outlet end.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
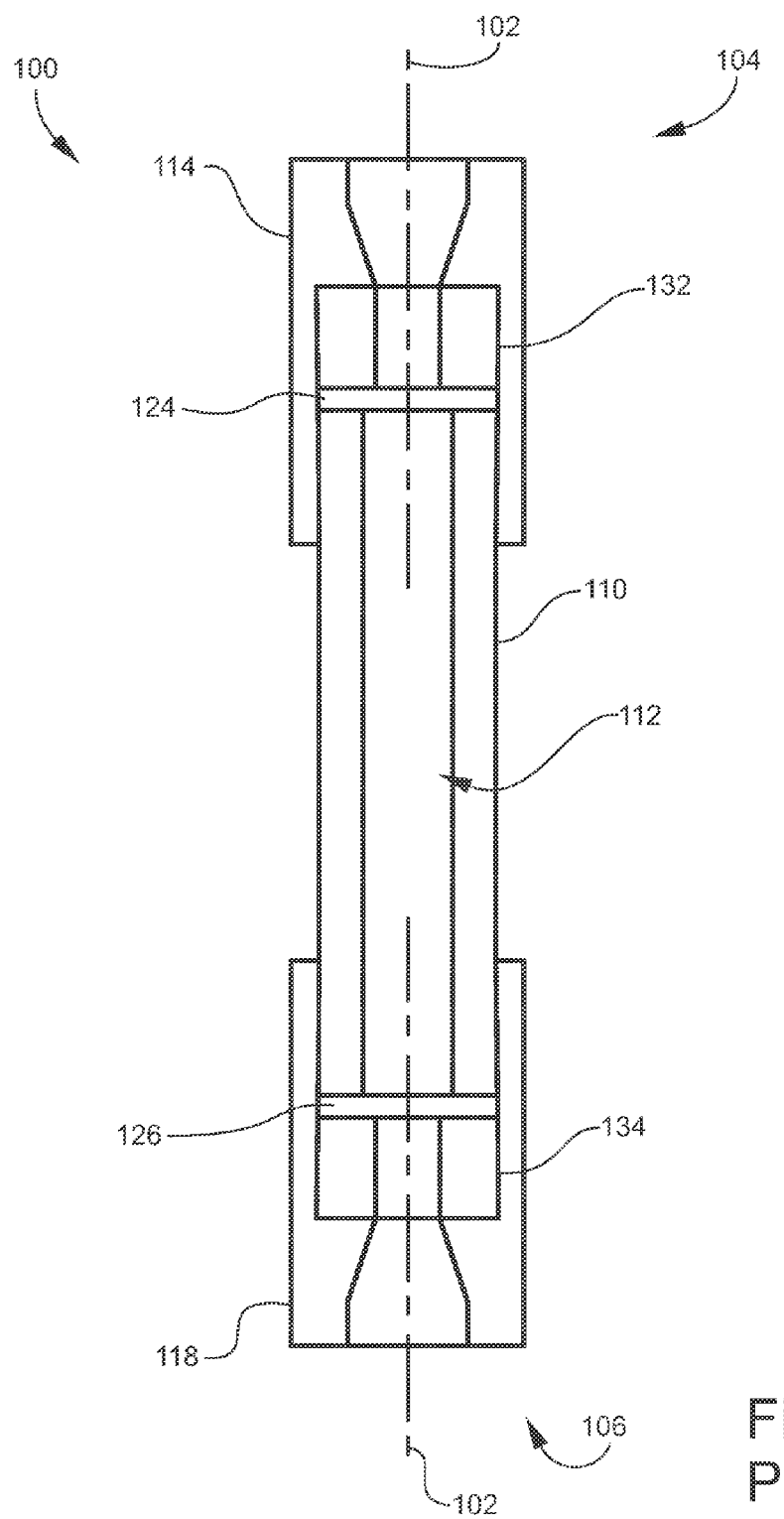
FIG. 1 is a cross-sectional view of an example of a chromatography column of known configuration.

FIG. 1 is a cross-sectional view of an example of a liquid chromatography (LC) column 100 of known configuration. The column 100 generally extends along a central (or longitudinal) axis 102 from a first column end 104 to a second column end 106. The features of the column 100 may be the same at the first column end 104 and the second column end 106, in which case the designation of which column end 104 or 106 serves as the inlet end or the outlet end is arbitrary. The column 100 generally includes a column wall 110 elongated along the axis 102 that encloses a column interior 112. The wall 110 is typically cylindrical (e.g., a tube) and thus the column interior 112 is typically a cylindrical bore between the column ends 104 and 106. The column 100 includes components at the column ends 104 and 106 for providing fluidic interfaces between the column interior 112 and tubing or other fluidic components external to the column 100. For example, the column 100 may include a first end fitting 114 securely engaging the wall 110 at the first column end 104, and a second end fitting 118 securely engaging the wall 110 at the second column end 106. In the present context, "securely engaging" generally means that the end fittings 114 and 118 will not become disengaged from the wall 110 during normal, intended operations of the column 100, including at the pressures typically contemplated for the specific type of chromatography being performed (e.g., HPLC, UHPLC, SFC, etc.) and at the generally higher pressures applied during the packing of the stationary phase media into the column. The end fittings 114 and 118 may be securely engaged to the wall 110 via the mating of complementary threads (not shown) on inside surfaces of the end fittings 114 and 118 and outside surfaces of the wall 110. Alternatively, the end fittings 114 and 118 may be securely engaged to the wall 110 by press-fitting, welding, brazing, etc. Each end fitting 114 and 118 includes a bore adapted for connection to the fluid lines of a chromatographic system. For example, the bore may include threads for engaging a fluid conduit fitting (not shown). Each bore is in fluid communication with the column interior 112 of the wall 110, whereby a fluid flow path is established from the first (inlet) column end 104 (inlet end), through the column interior 112 and to the second column end 106 (outlet end).

The column interior 112 extends from one axial end of the wall 110 to the opposite axial end of the wall 110. In the assembled form of the column 100, the column interior 112 contains (is filled with) a particulate packing material providing the stationary phase for chromatography. The column 100 may include retaining members, i.e., devices for retaining particles in place as a packed bed in the column interior 112, for example frits (or filters) 124 and 126. The frits 124 and 126 may be positioned at each axial end of the wall 110. The frits 124 and 126 provide axial boundaries holding the particulate packing material in place, yet include central porous sections to enable passage of the mobile phase/sample matrix. The column 100 may also include respective frit retainers 132 and 134 between the end fittings 114 and 118 and frits 124 and 126. Each frit retainer 132 and 134 includes a through-bore in fluid communication with the column interior 112 via the corresponding frit 124 and 126, thereby fluidly interconnecting the column interior 112 and the bores of the end fittings 114 and 118. The frit retainers 132 and 134 may provide fluid-tight interfaces between the end fittings 114 and 118 and the fits 124 and 126. After loading the column interior 112 with an appropriate amount of particulate material, assembly of the column 100 may entail screwing or otherwise securing the end fittings 114 and 118 onto the column 100. Axial movement of the end fittings 114 and 118 axially compresses the end fittings 114 and 118 against the frit retainers 132 and 134, which in turn axially compresses the frit retainers 132 and 134 against the fits 124 and 126 and the frits 124 and 126 against the axial ends of the column wall 110.

The column 100 illustrated in FIG. 1 is an example of a conventional, pure cylindrical configuration in which the inside surface of the column wall 110 is smooth and parallel to the central axis 102 at all points along the column length. The conventional configuration has disadvantages as noted above. The resolution of detected peaks from liquid chromatography columns packed with adsorption media depends on the internal structure of the media and how it affects the flow of the mobile phase through an LC column. Radial differences in the ratio of void volume to solid volume result in flow heterogeneity that increases the rate of analyte dispersion. The radial differences in packing structure are induced by the presence of the column wall, which acts to increase the ordered arrangement of particles that are closest to it.

According to the present disclosure, an LC column includes a column wall that is structured such that the inside surface of the wall has a variable slope, i.e., a variable radius from the central axis. The structured wall acts to eliminate the particle ordering common to conventional unstructured, pure cylindrical LC columns. Moreover, the structured wall changes the length of the fluid flow paths near the wall, thereby reducing the increased flow rates conventionally associated with nearness to the wall and hence reducing radial flow heterogeneity.

According to some embodiments, an LC column includes an inlet end, an outlet end, and a wall having a length along a central axis from the inlet end to the outlet end. The wall encloses a column interior in which a plurality of particles is packed, i.e., the column interior contains a particle packing. The wall (i.e., the inside surface of the wall) has a column radius relative to the central axis. The wall includes a structured portion configured such that the column radius varies over the length of the column. That is, as one moves along the axial direction from the inlet end to the outlet end (or vice versa), the column radius changes one or more times due to the provision of the structured portion. The structured portion is located at an axial position where at least some of the particles are in contact with the structured portion. With the inclusion of the structured portion, the LC column is not configured as a straight (or pure) cylinder, at least not so at the location of the particle packing.

The wall may have any composition, thickness, and length suitable for utilizing the wall as an analytical or preparative LC column. For example, the wall should be capable of repeatedly withstanding the internal pressures typically encountered in the LC technique being applied (HPLC, UHPLC, SFC), should be chemically inert to the materials transferred through the LC column, and should be long enough for the chromatographic operation contemplated. Thus, for example, the wall may be composed of a metal, metal alloy, polymer, glass, or ceramic suitable for LC. In some embodiments and as a non-limiting example, the column radius may be in a range of 0.5 mm to 15 mm, while in other embodiments the column radius may be greater than 15 mm. In some embodiments and as a non-limiting example, the column length may be in a range of 10 mm to 500 mm.

Generally, the dimensions of the structured portion are limited only by the overall dimensions of the wall. The structuring of the LC column wall may fall within three regimes or scales—micro, meso, or macro. The method employed for forming the structured portion may be selected or dictated by which regime characterizes the structured portion. The micro regime includes features (patterns, structures, etc.) that have at least one dimension on the order of the size of the particles to be packed into the column. For example, if the particles are 5 micrometers (μm) in size, a micro regime feature would be about that size as well. The meso regime includes features approximately 10 to 100 times larger than the particle size. The macro regime includes features larger than the meso regime. As an example, a feature created in an LC column wall that is approximately 250 μm across and 10 μm deep would be considered to be a meso feature.

In the present context, the "size" of a particle is its characteristic dimension. Typically, the characteristic dimension is taken to be the diameter of the particle. Given that a particle may be irregularly shaped or at least not shaped as a perfect sphere, the diameter may be taken to be the effective diameter, i.e., the diameter the particle would have if it were perfectly or substantially spherical. Moreover, no limitation is given as to the degree of polydispersity of the particles in the packed bed of an LC column as described herein. Thus, particle size may be interpreted as being the average size of the particles. In some embodiments, the particles have a size (or average size) within a range of 1.0 μm to 20 μm. The particles utilized in LC columns disclosed herein may have any properties (size, composition, porosity, functionalization, etc.) suitable for the LC application contemplated.

Depending on the fabrication technique employed, the structured portion may be considered as being integral with the column wall or as being a distinct component attached to the inside surface of the column wall in a permanent manner. As examples, the structured portion may be integrally formed by deforming or otherwise modifying an initially cylindrical wall, or by removing material from the wall, in which case the structured portion and the main portion may be considered as being part of the same monolithic structure. Alternatively the structured portion may be formed by adding material to the wall in a manner in which the resulting structured portion is observed to be an integral feature of the wall. Alternatively, the structured portion may be added to an initially cylindrical wall in a manner in which the structured portion is observed to be a feature distinct from other portions of the wall.

In some embodiments, the wall may be considered as including a main portion (or first portion) as well as the structured portion (or second portion). The main portion may be distinguished from the structured portion by the main portion having a radius from the central axis different from the radius of the structured portion. For example, the main portion may have a first radius and the structured portion may have a second radius different from the first radius. The second radius may be less than the first radius—that is, the structured portion may protrude into the column interior toward the central axis. Alternatively, the second radius may be greater than the first radius—that is, the structured portion may be a recessed portion of the wall having an inside surface spaced farther away from the central axis than the main portion. A recessed portion may be a portion of the wall that has been deformed, or a portion of the wall at which a recess has been formed into the thickness of the wall. In some embodiments, the main portion may be a non-structured portion. The non-structured portion may have a radius that is constant along the axial length of the wall—that is, all sections of the non-structured portion may have the same radius. In some embodiments, the non-structured portion may occupy the envelope of a straight cylinder whose geometry is interrupted by the structured portion. In all such cases, after forming the packed bed, at least some of the particles are in contact with the structured portion while other particles are in contact with the main portion.

In some embodiments, the structured portion may be considered as spanning or covering a part of the inside surface of the wall (or a part of the main portion of the wall). When formed by adding material, the composition of the structured portion may be the same as or different from that of the other portions of the wall.

Generally, the structured portion may include any feature or profile that results in a varied column radius. The structured portion may include any type of protrusion or raised feature (e.g., boss, ridge, mesa, etc.) or recess or indented feature (e.g., depression, pocket, dimple, trough, channel, groove, flute, etc.). The structured portion (or a feature of the structured portion) may include any type of shape or profile. Examples of shapes or profiles include, but are not limited to, rounded (e.g., circular, elliptical, semicircular, hemispherical, parabolic, hyperbolic); polygonal (e.g., square, rectilinear, rhomboidal, pyramidal, trapezoidal, star-shaped, cross-shaped); a combination of rounded and polygonal elements (e.g., conical, frustoconical, polygonal with rounded ends or sides); and irregular shapes. The structured portion may have a predominant dimension (may be elongated) in any direction relative to the central axis. The structured portion may be elongated in the axial direction, e.g., a channel parallel to the central axis. The structured portion may be elongated in the circumferential or arc direction, e.g., a ring or band coaxial with the central axis. The structured portion may follow a helical path (or other twisted or curved path) along the wall over one or more turns relative to the central axis. The helical path may have a constant or varying pitch (distance between turns). The structured portion may be elongated in more than one dimension, such as a cross shape.

Whether straight or curved, an elongated structured portion may span a significant axial distance (from one end to the other end of the structured portion) over the length of the wall. For example, the structured portion may span an axial distance of greater than 50% of the length of the wall. Such structured portion may be referred to as a "continuous" structured portion. A continuous structured portion may also span the entire length or substantially the entire length of the wall. Alternatively, the structured portion may be localized to a smaller region of the wall. Moreover, a structured portion may follow a lengthy path along the length of the wall but be discontinuous, i.e., segmented into discrete sections spaced from each other along the path.

The structured portion may include a plurality of discrete structured sections or units distributed over one or more regions of the wall. The structured sections may be uniformly spaced from each other or non-uniformly spaced from each other, i.e., the spacing between some adjacent pairs of structured sections may be different from the spacing between other adjacent pairs of structured sections. The structured portion may include two or more distinct groups of structured sections where the groups are spaced from each other. For example, each group may be spaced from an adjacent group by a distance greater than the spacing between the individual structured sections of the group. The structured sections of the structured portion may be arranged in a linear (one-dimensional) array or a two-dimensional array with respect to the wall surface, or according to any other desired pattern of features. The structured sections may all have a uniform configuration. That is, the structured sections may all have the same attributes or features such as those described above, for example dimensions/size/regime (micro, meso, or macro); radius from central axis (protruding or recessed); shape or profile; continuous or localized; etc. Alternatively, one or more structured sections may have one or more attributes or features that are different from those of the other structured sections. Alternatively, the set of structured sections constituting the structured portion may be completely or substantially random in terms of their respective attributes or features.

Figure 2:
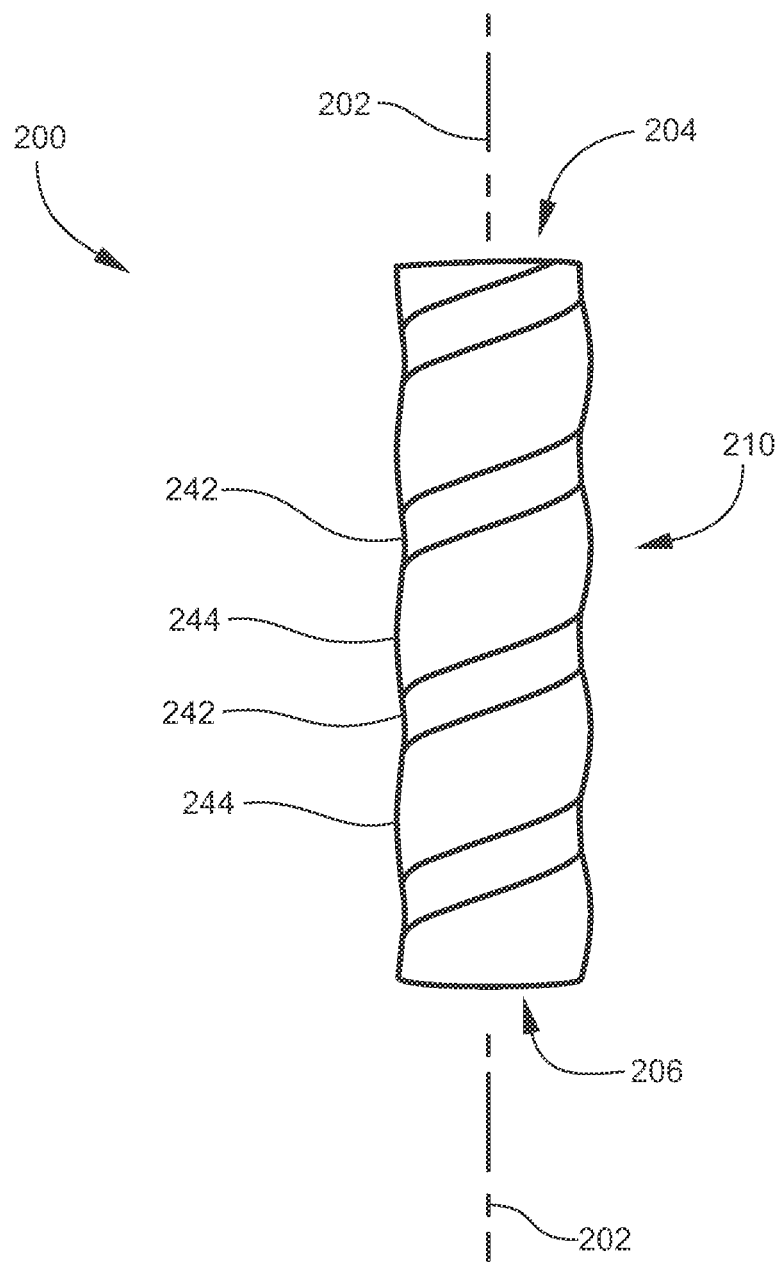
FIG. 2 is an elevation view of an example of a structured LC column according to some embodiments.

FIG. 2 is an elevation view of an example of a structured LC column 200 according to some embodiments. The LC column 200 includes an inlet end 204, an outlet end 206, and a column wall 210 having a length along a central axis 202 from the inlet end 204 to the outlet end 206. The wall 210 is generally configured as a tube and encloses a column interior. The wall 210 includes a main (or first) portion 242 having a first radius from the central axis 202 and a second, structured portion 244 having a second radius from the central axis 202. In the illustrated embodiment, the structured portion 244 is a helical structure that runs continuously through a number of turns from the inlet end 204 to the outlet end 206. In other embodiments, the helical structured portion 244 may run along only a part of the length of the wall 210. In the illustrated embodiment, the radius of the helical structured portion 244 (second radius) is greater than the first radius. In other embodiments, the second radius may be less than the first radius, i.e., the helical structured portion 244 may be a raised portion protruding inward in a manner analogous to an internal screw thread. The width of the helical structured portion 244 may be either meso or macro in scale. In the illustrated embodiment, the width is constant over its length from end to end, and its pitch is constant. In other embodiments, the width may vary and/or the pitch may vary. Also in other embodiments, the helical structured portion 244 may be discontinuous, i.e., may be partitioned into segments spaced from each other along the helical path. Also in other embodiments, the helical structured portion 244 may include two or more individual helical sections, i.e., the helical structured portion 244 may be characterized as having a multi-start or multi-threaded configuration.

Figure 3:
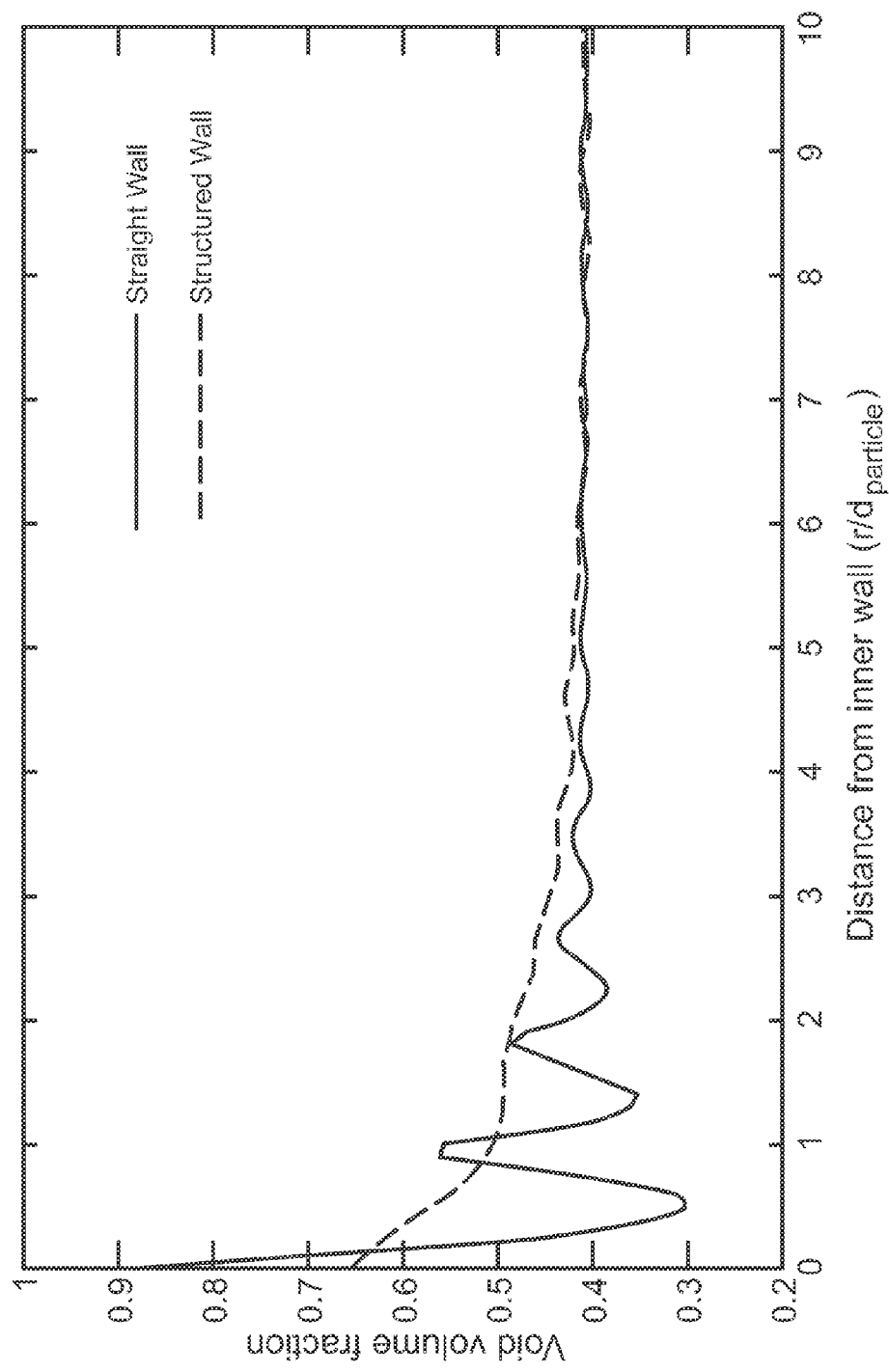
FIG. 3 is a plot of void volume fraction as a function of distance from the inside surface of an LC column wall for both the case of a conventional straight-walled column and a structured wall column as illustrated in FIG. 2.

As described above, an LC column with a structured wall such as illustrated in FIG. 2 provides advantages by eliminating or at least significantly reducing the particle ordering that would otherwise occur at and near the wall. This behavior was verified by computational simulations of particulate packing in a column with a helical structured portion as illustrated in FIG. 2, in comparison to a column having the same overall dimensions but with a straight cylindrical wall as illustrated in FIG. 1. The data is provided in FIG. 3, which is a plot of void volume fraction as a function of distance from the inside surface of the wall (expressed as radial distance r divided by particle diameter d) for both the straight wall and structured wall cases. The radial profile of the void volume fraction, averaged over the length of the column, demonstrates the effect of the structured wall. It can be seen that the structured wall eliminates the oscillations that occur with the highly ordered arrangement of particles along a straight column wall.

Figure 4A:
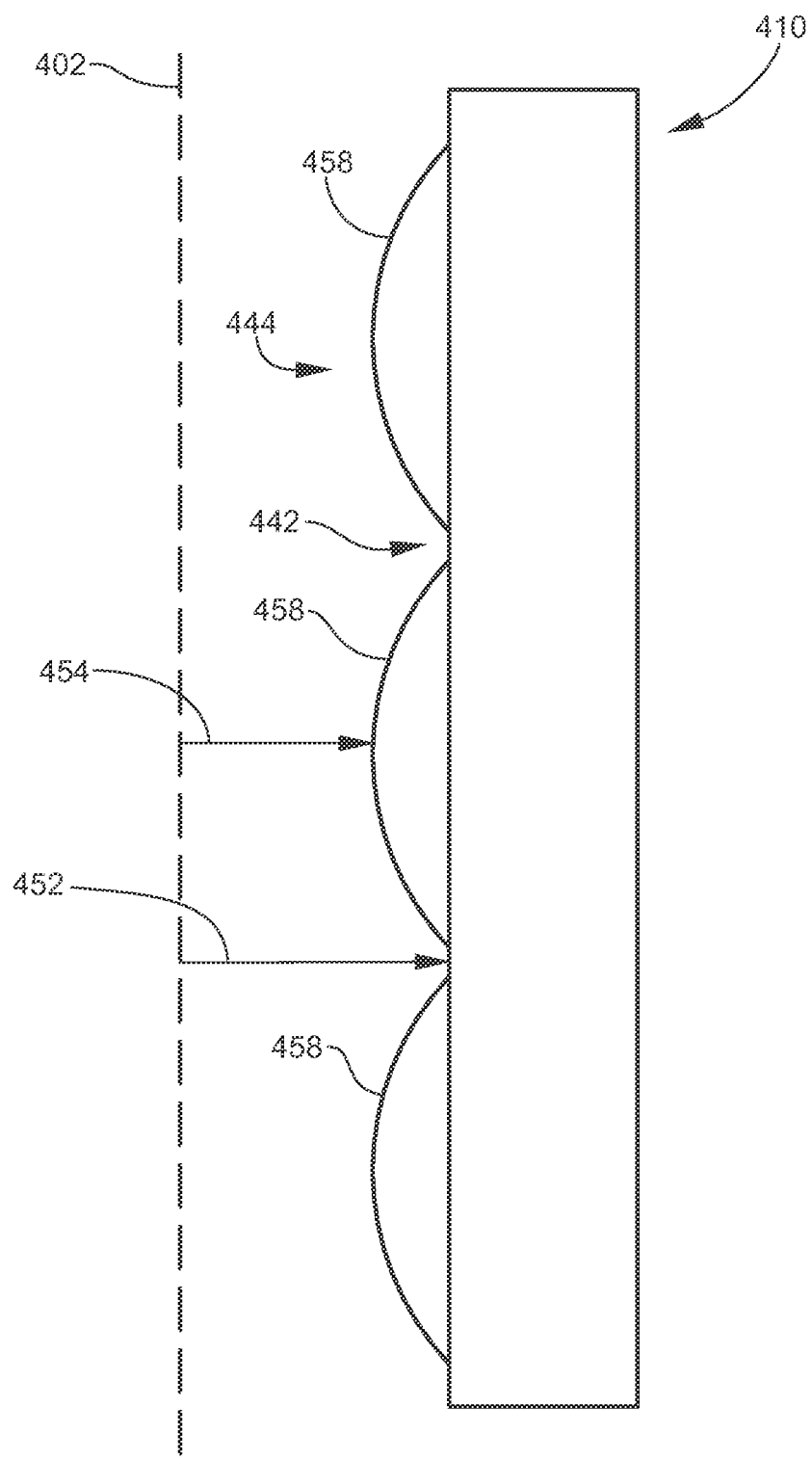
FIG. 4A is a cross-sectional elevation view of an example of a wall (or section of the wall) of an LC column according to another embodiment.

FIG. 4A is a cross-sectional elevation view of an example of a wall 410 (or section of the wall 410) of an LC column according to another embodiment. The wall 410 is coaxial with a central axis 402 running through the LC column. The wall 410 includes a main portion 442 having a first radius 452 from the central axis 402 and a structured portion 444 having a second radius 454 from the central axis 402. The structured portion 444 includes a plurality of structured sections 458. The structured sections 458 are raised sections, or protrusions. Hence, the second radius 454 is less than the first radius 452. It will be noted that each structured section 458 has a profile having a radius that varies over a range of values, i.e., each structured section 458 may have one or more radii different from the first radius 452. In this case, the "second radius" 454 may be taken to be the radius having the lowest value, which in the illustrated embodiment occurs at the apex of the dome-shaped structured section 458. Each structured section 458 may be continuous along the inner circumference of the wall 410, i.e., may be a band or ring. Alternatively, multiple structured sections 458 may be circumferentially spaced from each other, which arrangement may be repeated at one or more different axial positions along the length of the wall 410 (e.g., the three axial positions at which profiles are illustrated in FIG. 4A).

Figure 4B:
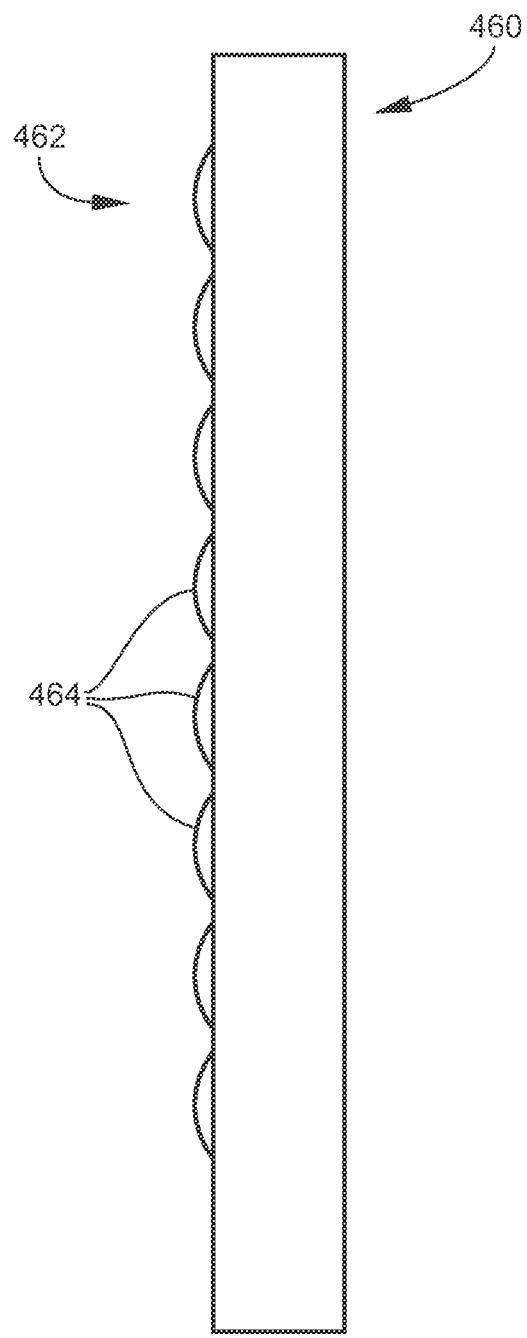
FIG. 4B is a cross-sectional elevation view of another example of a wall (or section of the wall) of an LC column according to another embodiment.

FIG. 4B is a cross-sectional elevation view of another example of a wall 460 (or section of the wall 460) of an LC column according to another embodiment. The wall 460 includes a structured portion 462 similar to that shown in FIG. 4A. The difference is that the structured portion 462 in FIG. 4B includes a greater number of structured sections 464 along the length of the wall 460. These structured sections may or may not be smaller than those shown in FIG. 4A.

Figure 5A:
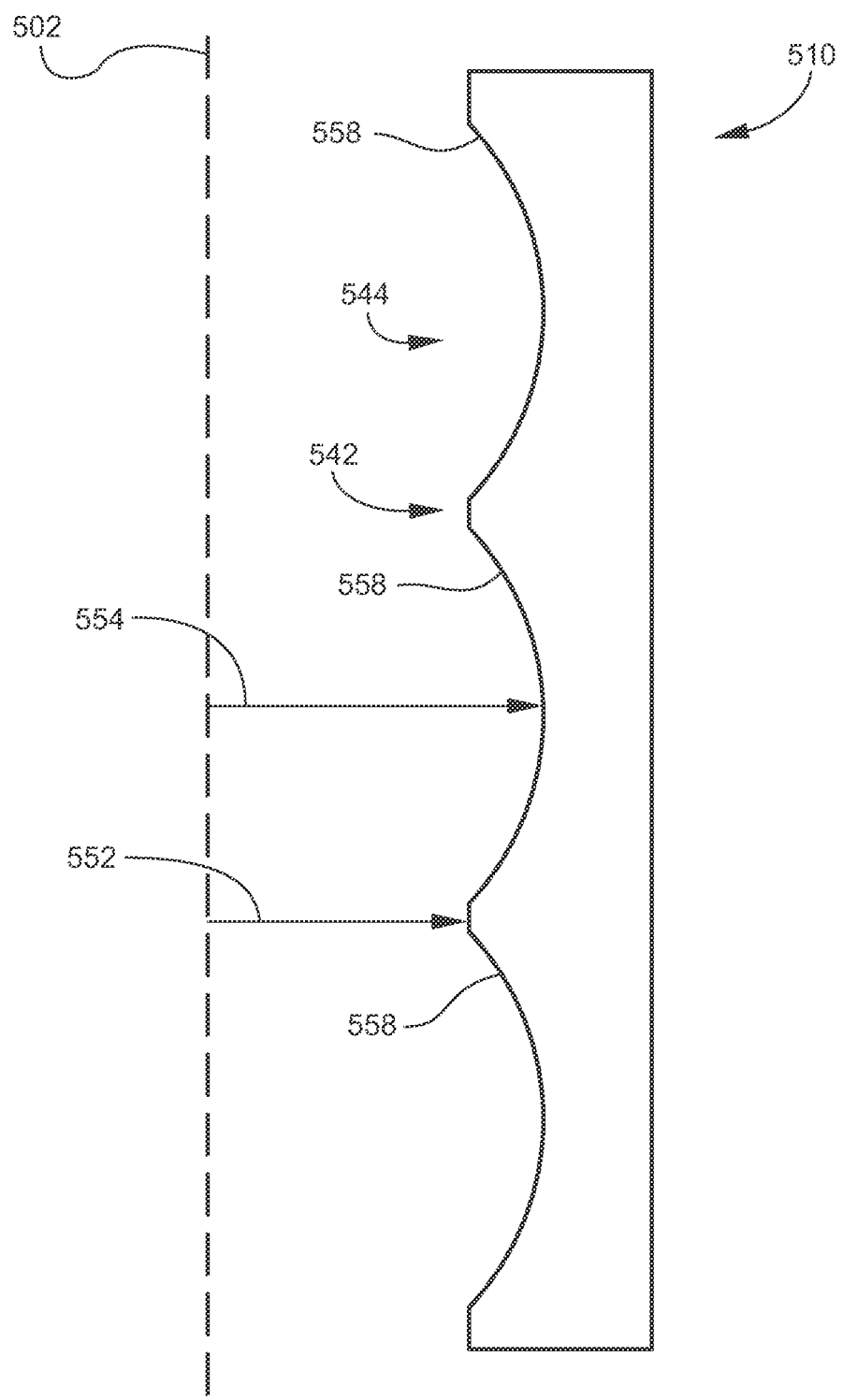
FIG. 5A is a cross-sectional elevation view of an example of a wall (or section of the wall) of an LC column according to another embodiment.

FIG. 5A is a cross-sectional elevation view of an example of a wall 510 (or section of the wall 510) of an LC column according to another embodiment. The wall 510 is coaxial with a central axis 502 running through the LC column. The wall 510 includes a main portion 542 having a first radius 552 from the central axis 502 and a structured portion 544 having a second radius 554 from the central axis 502. The structured portion 544 includes a plurality of structured sections 558. In this embodiment, the structured sections 558 are recesses or indentations formed into the thickness of the wall 510. Hence, the second radius 554 is greater than the first radius 552. The attributes of the structured portion 544 and possible alternative attributes may otherwise be similar to those described above in conjunction with FIG. 4A.

Figure 5B:
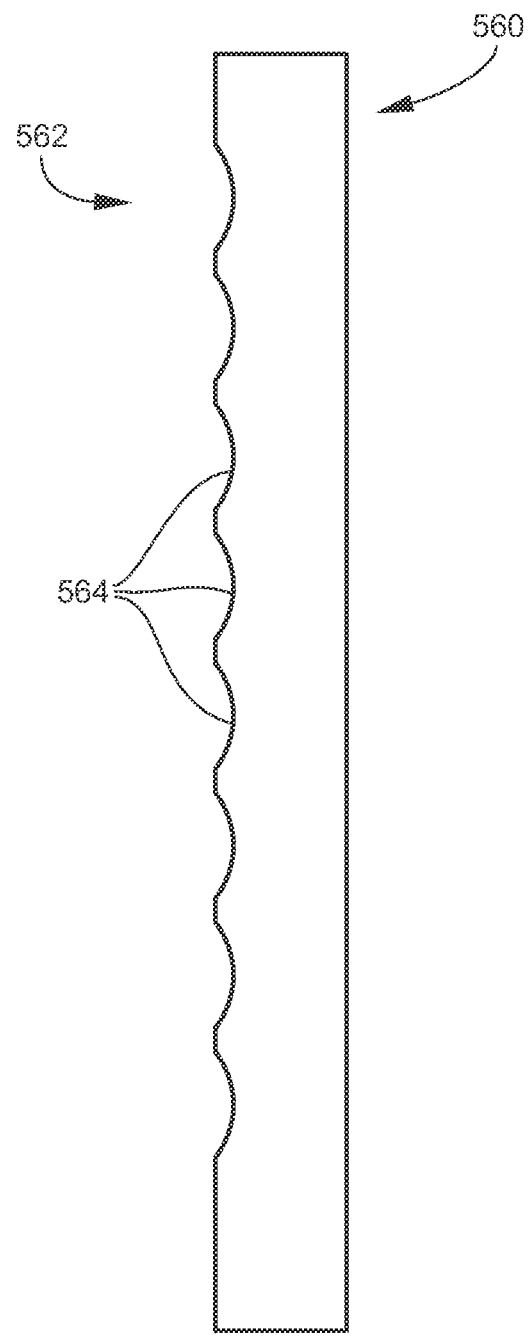
FIG. 5B is a cross-sectional elevation view of another example of a wall (or section of the wall) of an LC column according to another embodiment.

FIG. 5B is a cross-sectional elevation view of another example of a wall 560 (or section of the wall 560) of an LC column according to another embodiment. The wall 560 includes a structured portion 562 similar to that shown in FIG. 5A. The difference is that the structured portion 562 in FIG. 5B includes a greater number of structured sections 564 along the length of the wall 560. These structured sections 564 may or may not be smaller than those shown in FIG. 5A.

Figure 6A:
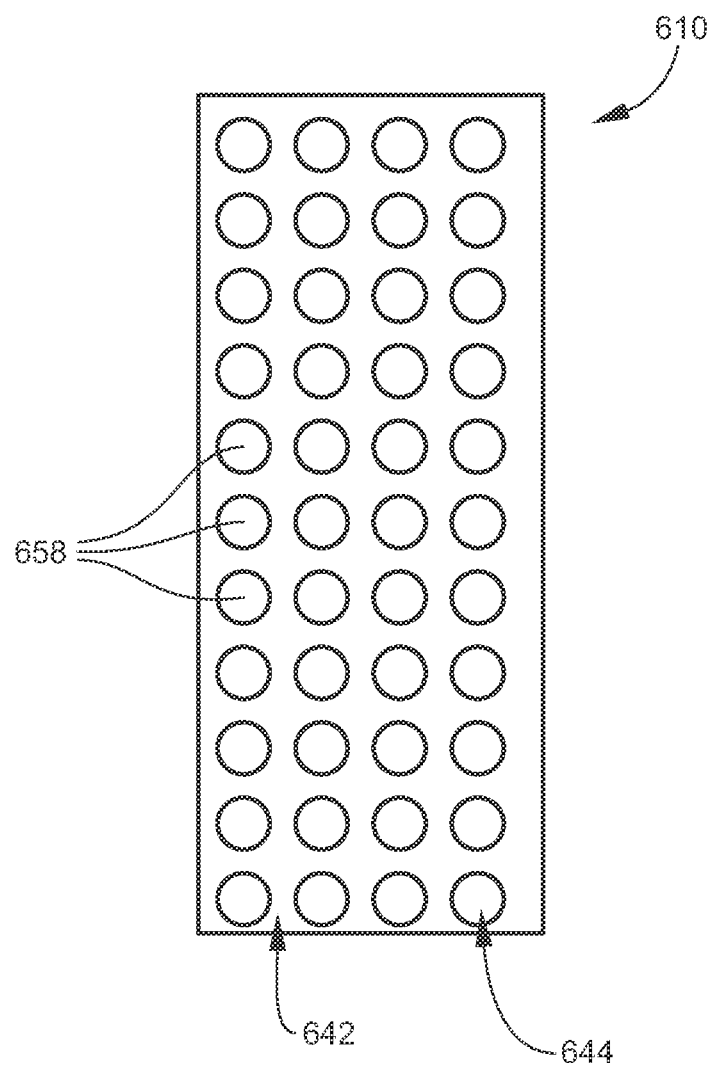
FIG. 6A is a planar projection view of an example of a wall (or section of the wall) of an LC column according to some embodiments.

FIG. 6A is a planar projection view of an example of a wall 610 (or section of the wall 610) of an LC column according to some embodiments. The view is from the perspective of the column interior. The wall 610 includes a main portion 642 having a first radius from the central axis and a structured portion 644 having a second radius from the central axis. The structured portion 644 includes a plurality of structured sections 658. The structured sections 658 may be protrusions, or recesses, or a combination of both protrusions and recesses. As non-limiting examples, the structured sections 658 may have profiles such as shown in any of FIGS. 4A to 5B. In this embodiment, the structured sections 658 are arranged in a two-dimensional array (rows and columns). The array may span the entire or substantially the entire inside surface of the wall 610, or a smaller portion thereof. The illustrated array (group of structured sections 658) may be representative of one of a plurality of such arrays. That is, the structured portion 644 may include two or more such arrays located at different sections of the wall 610. In this embodiment, the structured sections 658 may be considered as being "local" features in that the dimensions of the structured sections 658 are small relative to the overall dimensions of the wall 610. By this configuration, multiple local structured sections 658 may be positioned along a given dimension or direction of the wall 610 (e.g., axial direction, arc direction or circumference, etc.). In other embodiments, the structured sections 658 may be arranged in a linear array (e.g., include just one row or column) that may follow a straight or helical path.

Figure 6B:
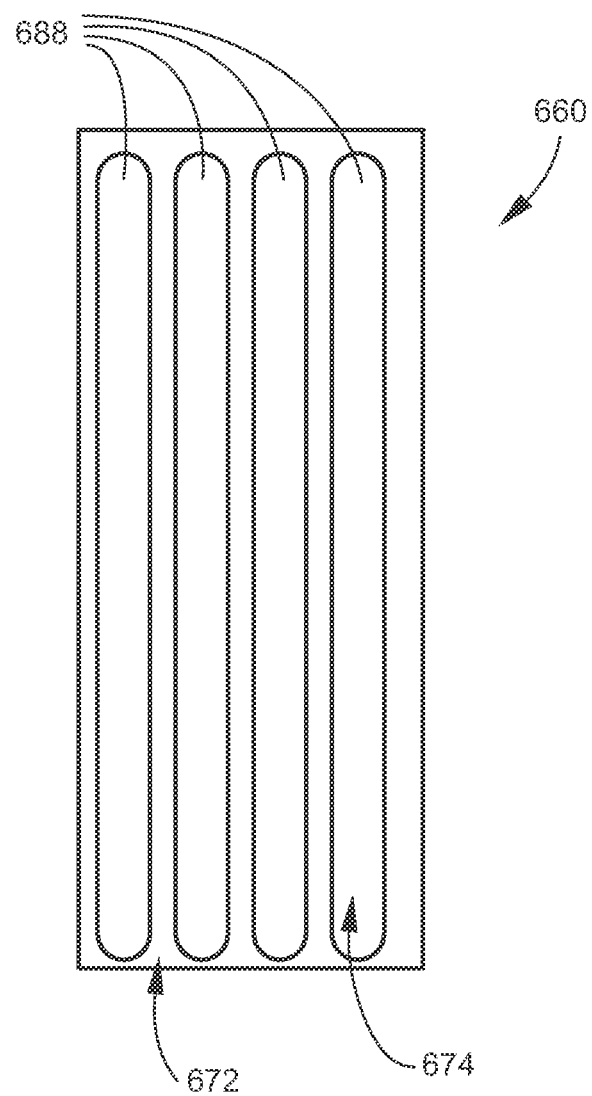
FIG. 6B is a planar projection view of an example of a wall (or section of the wall) of an LC column according to other embodiments.

FIG. 6B is a planar projection view of an example of a wall 660 (or section of the wall 660) of an LC column according to other embodiments. The view is from the perspective of the column interior. The wall 610 includes a main portion 672 having a first radius from the central axis and a structured portion 674 having a second radius from the central axis. The structured portion 674 includes a plurality of structured sections 688. The structured sections 688 may be protrusions, or recesses, or a combination of both protrusions and recesses. As non-limiting examples, the structured sections 688 may have profiles such as shown in any of FIGS. 4A to 5B. In this embodiment, the structured sections 688 are arranged in a linear array. The array may span the entire or substantially the entire inside surface of the wall 660, or a smaller portion thereof. The illustrated array (group of structured sections 688) may be representative of one of a plurality of such arrays. That is, the structured portion 674 may include two or more such arrays located at different sections of the wall 660. In this case, the structured portion 674 may be considered as being a two-dimensional array, with the set of individual structured sections 688 illustrated in FIG. 6B being one row or column of the array. In the illustrated embodiment, the structured sections 688 may be considered as being continuous or elongated features in that at least one dimension (e.g., axial length or circumferentially) of the structured sections 688 are large relative to a corresponding dimension of the wall 660. The structured sections 688 may follow a straight path as illustrated or alternatively may follow a helical path.

In other embodiments, the structured portion of a wall of an LC column as disclosed herein may include a combination of different features described herein, such as, for example, those illustrated in FIGS. 2 and 4A to 6B.

It will be understood that LC columns disclosed herein, such as those illustrated in FIGS. 2 and 4A to 6B, may include other components as necessary for providing a fully assembled column ready for use in chromatographic operations. Some examples of such other components are described above in conjunction with FIG. 1, e.g., retaining members for the particle packing, end fittings suitable for coupling to fluidic lines, etc.

Structured LC columns as disclosed herein may be fabricated by various methods. As one non-limiting example, a column wall is formed such that includes an inlet end, an outlet end, and a length along a central axis from the inlet end to the outlet end. The wall encloses a column interior and has a column radius relative to the central axis. A structured portion is formed on the inside of the wall such that it includes features facing the column interior. The structured portion is configured such that the column radius varies along the column length. A particle packing is then formed in the column interior such that at least some of the particles are in contact with the structured portion. The particle packing may then be secured and the assembly of the column finalized by known techniques.

Generally, the structured portion may be formed by removing material from the wall, adding material to the wall, modifying (e.g., deforming) the wall, or a combination of two or more of the foregoing. The specific fabrication method utilized may depend on a number of factors, such as the type of structural features desired, the size of the structural features desired (micro, meso or macro regime), and the compatibility of the method with the desired column material. The structured portion may be formed during the process of forming the wall. For example, a material addition process may be utilized to form the base structure of the wall (e.g., a column of pure cylindrical geometry) and simultaneously form the structured portion of the wall. A material addition process may also be utilized to first form the base structure of the wall and to subsequently form the structured portion of the wall, with the two formation steps being carried out in the same chamber. The material addition process utilized to form the base structure may be the same as or different from the material addition process utilized to form the structured portion. Additionally, various processes entailing the use of a mold may be utilized to form the base structure and structured portion simultaneously. Alternatively, the wall may first be formed to have a nominal, pure cylindrical geometry (or initially provided as an off-the-shelf LC column), and thereafter may be separately processed to form the structured portion.

Material removal may be carried out, for example, by machining. Machining may entail, for example, operating one or more cutters to remove material from the inside surface of the column wall to form the desired pattern of structural features. The cutter(s) may be controlled by a programmable instrument such as a CNC (computer numerical controlled) lathe. The use of cutters is suitable, for example, for forming continuous features such as spirals or helices. Another example of machining is broaching, which is particularly suitable for forming continuous features parallel with the column axis.

Another example of material removal is laser ablation and/or laser melting, in which a laser beam is focused through the column wall to pattern the inside wall surface. Such laser-based methods are mainly limited to optically clear column materials that allow the laser beam to be focused through the wall from the outside. A system with a controllable laser turning mirror on the inside of the column may be utilized, which allows the laser beam to be directed through one of the open axial ends of the column to the mirror.

Additional examples of material removal methods entail etching by chemical (wet etching), electrical, or electro-chemical means. Typically, such methods entail the use of a patterned mask or other means for defining a pattern on the inside wall surface that dictates where material will be removed (by etching) and where material will not be removed.

For instance, lithography may be employed in conjunction with etching, particularly in the case of glass columns. A suitable photoresist is applied to the inside wall surface and patterned by a known technique. After the pattern is defined, a technique based on chemical (wet etching), electrical, or electro-chemical is carried out to etch the areas of the inside wall surface exposed through the photoresist to the etchant introduced into the column interior.

As an alternative to a patterned mask, an insert can be created such that it defines the locations for the chemical, electrical, or electro-chemical based material removal. For example, if a series of deep patterns are defined on the exterior surface of a cylindrical rod that has a diameter just small enough to fit inside the LC column, the patterns would allow access of the material removal means to the LC column wall but not allow access in areas where the cylindrical rod has not been patterned.

As an additional alternative, the locations of material removal may be controlled using a shaped insert that is placed inside the LC column. An electrical or electro-chemical technique is then employed to remove material. In this case, the shape of the insert defines the electric field within the column during material removal and thereby defines the locations and material removal rates over the inside surface of the column wall.

As an additional alternative, electro-discharge-machining (EDM) may be utilized in conjunction with a shaped insert to remove material from, for example, a metal column wall by EDM-based cutting in accordance with the pattern defined by the shaped insert.

A further method for controlling the locations of material removal utilizes sequential plugs of liquid inserted in the column such that some of the plugs are made up of liquid that etches the wall material and other plugs are made up of liquid that does not. Material removal in this case may be effected by chemical or electro-chemical means. Such a method may be particularly suitable for forming ring-shaped features of controllable widths (in the axial direction).

Material modification or deformation may be carried out, for example, by embossing, a specific example of which is described further below. The embossing method does not cut material but instead pushes a tool, commonly a hardened steel ball, along a desired path against the inside surface of the column wall with enough force such that the ball deforms the wall surface, resulting in one or more indentations in accordance with the desired pattern. In general, this ball-forming indentation method results in a smooth wall surface. Embossing is suitable, for example, for forming continuous features such as spirals or helices. An alternative indentation method may be performed on the inner wall of the column by deforming the outside of the column, which avoids having to contact the inside wall surface during the feature generation. A second method of embossing utilizes a hard, rigid mandrel that is inserted into the column, the mandrel has structures on its exterior that form the negative of the desired structures on the inside of the column wall, and the column with the mandrel inside it is rolled between two plates that deform the column such that the interior surface of the column is pressed onto the mandrel and thereby embossed with the structure shapes on the mandrel.

Material adding methods generally involve some method for creating a pattern of features to be generated on the inside wall surface. Patterns may be created, for example, by lithography, use of a shaped or patterned insert, and deposition of a mask by imprinting. Once the inside wall surface has been masked, various deposition or coating processes may be utilized to add material, including those commonly associated with microfabrication (e.g., microelectronics fabrication, micro-electro-mechanical systems (MEMS) fabrication, etc.). Depending on the specific process technique, deposition may be carried out at atmospheric pressure or in vacuum. Examples include, but are not limited to, evaporation, physical vapor deposition (PVD) (e.g., sputtering, ion plating), chemical vapor deposition (CVD), vapor phase epitaxy (VPE), and molecular beam epitaxy (MBE). Alternatively, liquid-phase and solution-process based methods may be utilized to create three-dimensional features, such as, for example, electro-plating, dip coating, spray coating, and ink printing. An instrument such as a dip pen or an atomic force microscope (AFM) may be utilized to add material to the inside wall surface.

An alternative method for creating the mask on the inside wall surface utilizes surface property modification through direct patterned chemical surface modification or through a material that is deposited in a pattern on the wall. One example is the use of an imprinted material such as PTFE (polytetrafluoroethylene) that is hydrophobic while the inside wall surface is hydrophilic. A deposited material will then preferentially deposit on one or the other surface but not both.

Additionally, a self-assembling material technology may be implemented to create features that form autonomously with the desired shapes and sizes.

Additionally, a mandrel may be formed such that it defines the empty space within the desired LC column. The mandrel is used as a mold such that the outer surface of the mandrel defines the structures and features on the inside wall surface of the final LC column. The advantage of this method is that it is comparatively easy to define features on the outside of a cylinder compared to defining features on the inside of a cylinder. Once the mandrel has been formed, electroplating may be used to create the LC column around the mandrel. Alternatively, another forming technology such as powder metallurgy or injection molding may be used. Once the column has been formed, the mandrel may be removed.

EXAMPLE

Figure 7A:
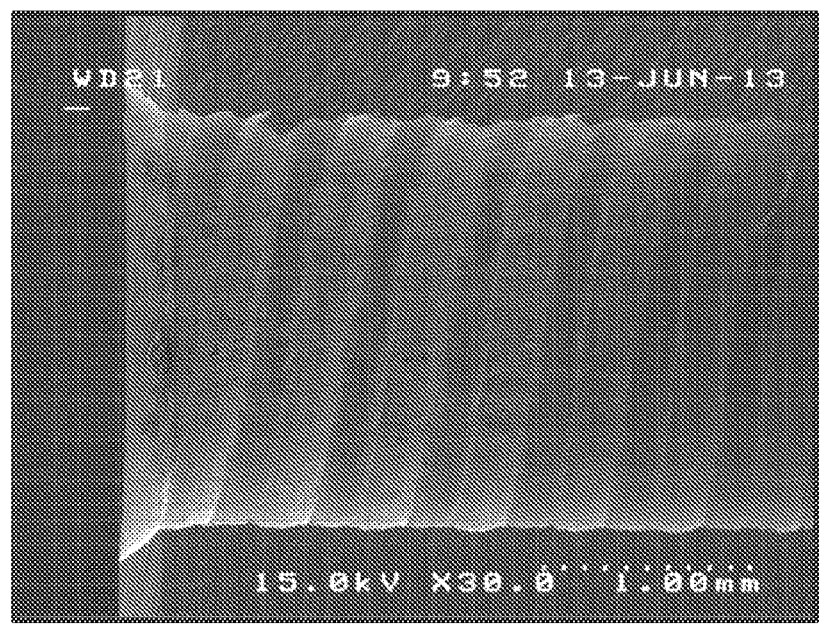
FIGS. 7A and 7B are SEM (scanning electron microscope) micrographs of the inside surface of a structured LC column fabricated in accordance with the present disclosure.
Figure 7B:
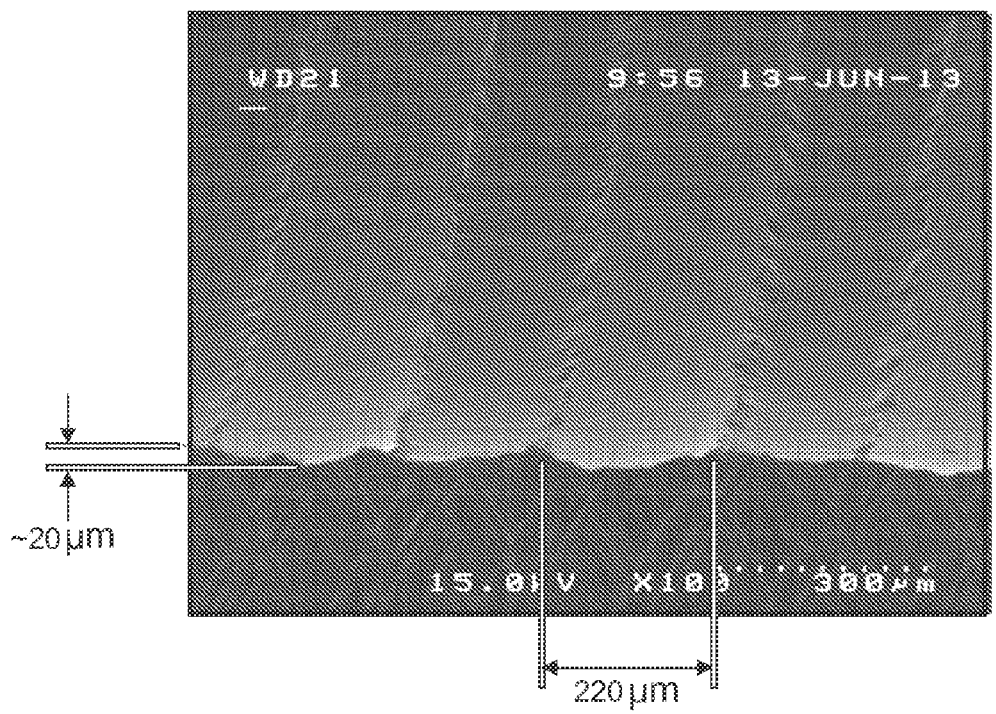

An LC column was fabricated to provide a continuous helical feature analogous to that illustrated in FIG. 2. FIGS. 7A and 7B are SEM (scanning electron microscope) micrographs of the inside surface of the LC column. The LC column had a length of 150 mm and an inside diameter of 2.1 mm. The LC column was initially provided as a standard, straight cylindrical column. The helical feature was formed as an indentation. The helical feature had a width of about 220 μm, and a radius (from column center) about 20 μm greater than that of the non-indented portion of the column wall. The helical feature was formed by employing a ball-forming method. Specifically, two balls held a precise distance apart were spirally moved down the inside of the LC column using a CNC (computer numerical controlled) lathe. The LC column was then packed with 1.8 μm diameter ECLIPSE PLUS™ particles commercially available from Agilent Technologies, Inc., Santa Clara, Calif.

In further embodiments, the present disclosure encompasses LC systems that include structured LC columns as disclosed herein. As one non-limiting example, an LC system may further include one or more additional components such as, for example: a source of one or more solvents upstream of the column for use as a mobile phase; a sample injection system for introducing a sample (sample material dissolved in a sample solvent) into the solvent flow stream (upstream of the column or at the column head); a collection site downstream of the column for collecting compounds separated by the column; and a system controller. The LC system may include various fluidic lines (tubing, channels, etc.) coupled to various components via fluid-tight fittings or other suitable means. The collection site may include a detector for detecting the compounds as they elute from the column. The detector may be any type suitable for enabling chromatographic peak data to be acquired and processed by the system controller. The system controller may control various components of the LC system. The system controller is typically an electronic processor-based controller. The structure and operation of various types of LC systems, and of the individual components typically utilized in such systems, are generally understood by persons skilled in the art and thus need not be further described herein.

Structured LC columns and associated LC systems as described herein may be configured for low-pressure and/or high-pressure LC. When configured for high-pressure LC, the LC columns and associated LC systems may be configured for high performance liquid chromatography (HPLC), ultra high performance liquid chromatography (UHPLC), or supercritical fluid chromatography (SFC). Accordingly, in the present disclosure the term "liquid" encompasses not only liquids as conventionally defined (e.g., in the liquid phase region of pressure-temperature space) but also supercritical and near supercritical fluids. As used herein, a "near supercritical" fluid is a fluid at a pressure and/or temperature state that places the fluid outside of, but near to, the supercritical region of a pressure-temperature phase diagram for that fluid. A near supercritical fluid may, for example, be a highly compressed liquid at a temperature less than the critical temperature demarcating the supercritical phase. The terms "low-pressure" and "high-pressure" are used herein in a relative sense to describe the pressure at which a liquid flows in an LC system, including the flow through a chromatography column of the system. As non-limiting examples, low-pressure flow may range from 0 bar to 20 bar and high-pressure flow may range from 20 bar or greater. In the case of supercritical fluid chromatography (SFC), high-pressure flow may range from 50 bar or greater.

Structured LC columns and associated LC systems as described herein may be configured for analytical chromatography or preparative chromatography. In analytical separation, the components are separated to facilitate their analysis by detection and data acquisition techniques. Analytical separation typically entails the use of a small amount of material and small inside-diameter columns (e.g., less than 1 inch). In preparative separation, the components are separated to purify or isolate one or more chemical components from the starting material, which may be done for a further use such as reaction, synthesis, etc. Preparative separation may be performed on a small scale comparative to analytical separation, or may be performed on a much larger scale to purify a large quantity of sample material, and thus may utilize larger inside-diameter columns (e.g., 1-24 inches).

Structured LC columns and associated LC systems as described herein may be configured for normal-phase chromatography, reversed-phase chromatography, or other types of chromatography involving the flow of a sample-bearing mobile phase through a column containing a packing or bed supporting a stationary phase. Structured LC columns and associated LC systems as described herein may further be configured for isocratic elution or gradient elution, and may be switchable between these two modes of operation.

It will be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A liquid chromatography (LC) column, comprising:
an inlet end;
an outlet end;
a wall having a length along a central axis from the inlet end to the outlet end, the wall enclosing a column interior and comprising a main portion and a structured portion, wherein the structured portion comprises a helical structure, and the helical structure is continuous, or is partitioned into helical segments spaced from each other; and
a plurality of particles packed in the column interior, wherein at least some of the particles are in contact with the structured portion and other particles are in contact with the main portion.

2. The LC column of claim 1, wherein the structured portion and the main portion are monolithic.

3. The LC column of claim 1, wherein the structured portion is positioned on a part of the main portion.

4. The LC column of claim 1, wherein the structured portion has a composition different from the other portions of the wall.

5. The LC column of claim 1, wherein the structured portion has a configuration comprising at least one of:
- the structured portion protrudes into the column interior;
- the structured portion is recessed away from the central axis; or
- at least one part of the structured portion protrudes into the column interior, and another part of the structured portion is recessed away from the central axis.

6. A method for fabricating a liquid chromatography (LC) column, the method comprising:
- forming a wall comprising an inlet end, an outlet end, and a length along a central axis from the inlet end to the outlet end, wherein the wall encloses a column interior and comprises a main portion;
- forming a structured portion on the wall facing the column interior, wherein the structured portion comprises a helical structure, and the helical structure is continuous, or is partitioned into helical segments spaced from each other; and
- after forming the structured portion, forming a packing of particles in the column interior, wherein at least some of the particles are in contact with the structured portion and other particles are in contact with the main portion.

7. The method of claim 6, wherein forming the structured portion comprises performing a step selected from the group consisting of deforming the wall, removing material from the wall, depositing material on the wall, and a combination of two or more of the foregoing.

8. The method of claim 6, wherein forming the structured portion comprises inserting a mandrel into the column interior, the mandrel comprising a patterned outer surface, and pressing the wall against the patterned outer surface.

* * * * *

UNITED STATES PATENT AND TRADEMARK OFFICE
CERTIFICATE OF CORRECTION

PATENT NO. : 10,073,068 B2
APPLICATION NO. : 15/023240
DATED : September 11, 2018
INVENTOR(S) : Hongfeng Yin et al.

Page 1 of 1

It is certified that error appears in the above-identified patent and that said Letters Patent is hereby corrected as shown below:

On the Title Page

On the page 2, Column 2, under "Other Publications", Line 3, delete "Razing" and insert -- Rozing --, therefor.

In the Specification

Column 4, Line 46, delete "fits" and insert -- frits --, therefor.

Column 4, Line 54, delete "fits" and insert -- frits --, therefor.

Signed and Sealed this
Fourth Day of December, 2018

Andrei Iancu
*Director of the United States Patent and Trademark Office*